(12) United States Patent
Gunes et al.

(10) Patent No.: US 8,709,456 B2
(45) Date of Patent: Apr. 29, 2014

(54) LIQUID-FILLED PROTEIN-PHOSPHATIDIC ACID CAPSULE DISPERSIONS

(75) Inventors: Zeynel Deniz Gunes, Lausanne (CH); Jin-Mi Jung, Epalinges (CH)

(73) Assignee: Nestec S.A., Vevey (CH)

( * ) Notice: Subject to any disclaimer, the term of this patent is extended or adjusted under 35 U.S.C. 154(b) by 25 days.

(21) Appl. No.: 13/578,458

(22) PCT Filed: Feb. 11, 2011

(86) PCT No.: PCT/EP2011/052035
§ 371 (c)(1),
(2), (4) Date: Aug. 10, 2012

(87) PCT Pub. No.: WO2011/098560
PCT Pub. Date: Aug. 18, 2011

(65) Prior Publication Data
US 2012/0308627 A1    Dec. 6, 2012

(30) Foreign Application Priority Data

Feb. 15, 2010   (EP) ..................................... 10153574

(51) Int. Cl.
*A61K 9/00*    (2006.01)
(52) U.S. Cl.
USPC ........... 424/401; 424/400; 424/422; 424/450; 424/489
(58) Field of Classification Search
USPC .......................... 424/400, 401, 422, 450, 489
See application file for complete search history.

(56) References Cited

FOREIGN PATENT DOCUMENTS

EP           815743 A2 *   1/1998

OTHER PUBLICATIONS

McClements et al., Structural Design Principles for Delivery of Bioactive Components in Nutraceuticals and Functional Foods, Critical Reviews in Food Science and Nutrition, 49:6m 577-606.*
Written Opinion and International Search Report issued Jun. 5, 2011 for PCT/EP2011/052035.

* cited by examiner

*Primary Examiner* — Michael G Hartley
*Assistant Examiner* — Robert Cabral
(74) *Attorney, Agent, or Firm* — K&L Gates LLP

(57) ABSTRACT

The present invention generally relates to the field of membranes. In particular, the present invention relates to a composition comprising bodies surrounded by a membrane. The composition are for example edible compositions. One embodiment of the present invention relates to a composition containing an oily fraction, a hydrophilic fraction, and at least one body, wherein the body comprises a shell comprising several molecular layers of protein and at least one phosphatidic acid surfactant; and a content comprising an internal phase containing a hydrophilic component and/or a hydrophobic component. The composition may be used to protect a food product or to deliver specific properties to a product, for example.

15 Claims, 3 Drawing Sheets

LIQUID-FILLED PROTEIN-PHOSPHATIDIC ACID CAPSULE DISPERSIONS

CROSS REFERENCE TO RELATED APPLICATIONS

The present application is a National Stage of International Application No. PCT/EP2011/052035, filed on Feb. 11, 2011, which claims priority to European Patent Application No. 10153574.8, filed on Feb. 15, 2010, the entire contents of which are being incorporated herein by reference.

The present invention generally relates to the field of membranes. In particular, the present invention relates to a composition comprising bodies surrounded by a membrane. The compositions are for example edible compositions. One embodiment of the present invention relates to a composition containing an oily fraction, a hydrophilic fraction, and at least one body, wherein the body comprises a shell comprising several molecular layers of complexant molecules, the complexant molecules being protein and at least one lipidic phosphatidic acid surfactant; and a content comprising an internal phase containing a hydrophilic component and/or a hydrophobic component. The composition may be used to protect a food product or to deliver specific properties to a product, for example.

Hollow oil-in-water or water-in-oil capsules of controlled size and thickness for controlled delivery purposes are usually produced by the process of layer-by-layer adsorption of (poly)ionic species on the droplets of an emulsion (Sukhishvili S. A., Curr. Op. Coll. Int. Sci. 2005, 10, 37; Grigoriev D. O., Miller R., Curr. Op. Coll. Int. Sci. 2009, 14, 48; Peyratout C. S., Dahne L., Angew. Chem. Int. Edit. 2004, 43, 3762). That is a tedious multi-step process which is time-consuming, and most often involves washing steps between two successive adsorption steps with alternating sign of electrostatic charge (Decker G., Eckle M., Schmitt J., Struth B., Curr. Op. Coll. Int. Sci. 1998, 3, 32), depending on the application.

The main advantage of the layer-by-layer method is that it allows building a tailored composite multi-layer structure, forming the shell of a hollow capsule. Other methods reported that allow for a certain degree of control on the shell thickness are based on the use of a multiple emulsion, or on phase separation at the o/w interface (Grigoriev D. O., Miller R., Curr. Op. Coll. Int. Sci. 2009, 14, 48).

As for coacervation methods, their main drawback is the high sensitivity to process parameters and the inhomogeneous shell thickness. A uniform and controlled shell thickness can be achieved by interfacial polymerisation between small or polymeric surfactants, however, these methods usually require the removal of non-food organic solvents and monomers. A consequence of this is that the resulting capsules are generally not applicable for food-grade products.

For example, U.S. Pat. No. 5,843,509 describes the formation of submicron capsules using chitosan and oil-soluble lecithin by using acetone as an organic solvent.

It was the object of the present invention to improve the state of the art and, in particular, to provide a food grade composition comprising capsules with a controllable wall thickness of a few nanometers to far above 100 nm.

For oil-in-water or water-in-oil emulsions, thickness control of the capsule walls was never achieved for large values, i.e. from 1 nm to 1 mm.

Hence, the present inventors were surprised to see that they could provide a composition that can be fabricated in one facile step and that comprises food-grade bodies of tuneable composition, size, and shell thickness, based on the interfacial complexation between ionic species forming a membrane at oil/water interface.

Consequently, the present inventors could achieve the object of the present invention by the subject matter of the independent claims. The dependent claims further develop the idea of the present invention.

The inventors describe a method that uses at least one protein to fabricate in one facile step, food-grade capsules of tuneable composition, size, and shell thickness, based on the interfacial complexation between ionic species forming a membrane at oil/water interface.

More specifically, the protein forms a complex with a lipidic phosphatidic acid surfactant.

The method allows forming water-in-oil and oil-in-water capsules, and enables the encapsulation of certain oil-soluble or water-soluble small molecules, such as flavours.

The body size is set by the emulsification step when mixing oil and water, as was observed using microfluidic and batch emulsification methods. Its thickness can be controlled finely between a few nanometers up to the supermicron scale. High thickness values result in very high viscoelastic moduli (in shear, it can reach more than 1 Pa·m). Nevertheless the shell in the wet state remains to be highly flexible.

Consequently, if used in cosmetic or food products, the presence of capsules with a wall thickness in the micrometer range or smaller will not result in unwanted sensorial properties, such as grittiness.

Hence, one embodiment of the present invention is a composition containing an oily fraction, a hydrophilic fraction, at least one body, wherein the body comprises (1) a shell comprising at least 20 molecular layers of complexant molecules and (2) a content comprising an internal phase containing a hydrophilic component and/or a hydrophobic component.

The complexant molecules may be a protein and at least one lipidic phosphatidic acid surfactant.

Typically, the lipidic phosphatidic acid surfactant content amounts to at least 20% w/w of all lipidic surfactants present in the shell.

The lipidic phosphatidic acid surfactant content may also amounts to at least 50% w/w of all lipidic surfactants present in the shell.

The protein carries a positive or no net charge at the pH of the composition.

The composition and/or the body described in the present invention have the advantage that they fulfil the GRAS standard.

Generally recognized as safe (GRAS) is an American Food and Drug Administration (FDA) designation that a chemical or substance added to food is considered safe by experts, and so is exempted from the usual Federal Food, Drug, and Cosmetic Act (FFDCA) food additive tolerance requirements.

For example, no more than 0.1 weight-% of protein may be present in solubilised state in the oily fraction of the composition and/or no more than 10 weight-% of lipidic phosphatidic acid surfactants may be present in solubilised state in the hydrophilic fraction of the emulsion.

The protein and at least one lipidic phosphatidic acid surfactant may be complexed at the supramolecular level. This complexation contributes to the stability of the shell.

The resulting body may have a positive, a negative or no net charge.

Positive or negative net charges have the advantage, that the body can be functionalized by compounds with an opposite charge or that the bodies can be separated from the composition by charge separation. It may also contribute to avoid colloidal aggregation of capsules. Negative charge may be used to avoid undesired astringency in food products, depending on the food matrix, and the concentration and size of the capsules.

A neutral net charge has the advantage that the body will remain an integral part of the composition, even if it is contained in containers which may already have or develop a positive or negative charge, for example if friction is applied to the container.

The composition may be produced without the use of non-food organic solvents, except food-grade oils. Hence, the composition of the present invention does not contain non-food organic solvents or residues thereof. This has the advantage that the composition may be easily used for cosmetic or food applications, without the need to remove non-food organic solvents and without the risk of having some residual said organic solvents present in the composition.

Organic solvents are solvents containing carbon. For example, the composition of the present invention may be prepared without the use of organic solvents and/or does not contain organic solvents with a boiling point below 100° C., 90° C. or 80° C.

The composition of the present invention may be any kind of composition. Preferably it is a food grade composition or a food product.

For example, the composition may be an emulsion, e.g. a sub-micro-emulsion, a micro-emulsion or a macro-emulsion.

The emulsion may also be a double emulsion, e.g., for low calorie applications.

The emulsion may further be an ISAmulsion. ISAmulsions are for example described in detail in USPTO Patent Application 20080255247. The term 'ISAmulsion' describes the specific nature of the oil droplets containing a structure being Internally Self-Assembled, which is different from ordinary oil-in-water or w/o/w double emulsions, including nano- and microemulsions, in which the oil droplets do not have a nano-sized self-assembled structure with hydrophilic domains. The ISAmulsion droplets basically consist of oil droplets which have a self-assembled structure with hydrophilic domains. This structure can be of a lamellar liquid crystalline, or a lamellar crystalline, or of a reversed nature comprising the L2, the microemulsion, the isotropic liquid phase, the hexagonal, the micellar cubic, or the bicontinuous cubic phase. The structures in the oil phase can appear as a single nano-structure or as a mixture of different nano-structures.

Emulsions have the advantage that they are pleasant to consume and offer an attractive mouthfeeling.

Sub-micro emulsions have the advantage that they are optically transparent and have no cloudy appearance.

Depending on the intended purpose micro- or macro-emulsions may be preferred because each of these emulsions offer specific organoleptic properties.

As protein any protein may be used that carries a positive or no net charge at the pH of the composition protein. For example, the protein may be selected from the group consisting of β-lactoglobulin, for example β-lactoglobulin monomers or rods, β-lactoglobulin fibres or mixtures thereof; caseinates, whey protein isolates, whey protein microgels (Donato, Schmitt, Bovetto and Rouvet, International Dairy Journal 2009, 19, 295), soy proteins and combinations thereof.

The at least one body may be a substantially round capsule, an elongated capsule, a flat-shaped capsule or a fibre. The method of the present invention allows adjusting the shape of the body according to the needs in the final product.

If it is desired to use the body to transport or protect valuable oily or hydrophilic compounds a substantially round or round shape may be preferred, because this shape allows it to contain a maximum amount of content per surface.

Elongated capsules, flat shaped capsules of fibres offer the advantage of a large surface. This is in particular useful, if the surface is going to be functionalized. Moreover, the hydrodynamic interactions can be greatly increased within the emulsion owing to non-spherical capsule shapes, which makes these shapes suitable for controlling the product viscosity and texture.

The body contains an internal phase. This internal phase may represent at least about 0.01 Vol-%, preferably at least about 50 Vol-%, even more preferred at least about 90 Vol-% of the content of the body. For, example, the body may be filled completely with the internal phase.

The internal phase may consist of a single compound or may contain a mixture of compounds.

For example the internal phase may comprise one or more hydrophilic components. A hydrophilic component of the internal phase may be liquid or gaseous. Such physical conditions refer to room temperature and standard pressure.

Hydrophilic components may be selected from the group consisting of hydrophilic liquids, such as water, fruit juices, lemonades, alcoholic beverages, coffee liquors, coffee extracts, flavoured waters, proteins in solution or dispersion, enzymes in solution or dispersion, water-soluble vitamins in solution; or combinations thereof.

The internal phase may alternatively or additionally comprise one or more hydrophobic components. A hydrophobic component of the internal phase may also be liquid or gaseous.

For example, the internal phase may contain hydrophobic components selected from the group consisting of flavoured and/or fragranced oils, for example mint oil; essential oils; fish oil; oily compounds comprising omega-3 fatty acids; and/or omega-6 fatty acids.

Consequently, the bodies of the present invention may be used for several purposes. For example, they may be used
- to protect valuable food ingredients, for example, from oxidation,
- to avoid that functional ingredients, e.g., enzymes, are in direct contact with a food product,
- to mask undesired off-tastes,
- to avoid unwanted odour generation,
- to impart a specific taste to a product,
- to impart a specific mouthfeel to a product, or
- to provide a specific texture in a product.

The shell of the body may comprise protein carrying a positive or no net charge at the pH of the composition and at least one lipidic phosphatidic acid surfactant. The shell may also contain other polyelectrolytes, such as further proteins, for example.

The shell may also consist of proteins carrying a positive or no net charge at the pH of the composition and a lipidic phosphatidic acid surfactant.

Protein and the at least one amphiphilic surfactant may be present in any proportion that allows the formation of a stable shell. Suitable proportions may be determined by those skilled in the art by using routine experimentation.

For example, protein and the at least one lipidic phosphatidic acid surfactant may be used in a weight ratio in the range of 1:10 to 10:1, preferably 5:1 to 1:1.

The lipidic surfactant phosphatidic acid may have a partition coefficient (water/oil) smaller than 1:100 in ambient conditions. Such anionic lipidic surfactants have the advantage that they will be present almost exclusively in the oily fraction of the composition in soluble state and/or at the oil/water interface, provided that the volume fraction of the dispersed oil phase is sufficiently high. For example, lipidic phosphatidic acid surfactants may be e.g. an ammonium phosphatidic fatty acid, or a mixture of phosphatidic acids comprised, e.g., in lecithin, preferably lecithin YN.

For example, the shell of the body may comprise protein carrying a positive or no net charge at the pH of the composition and lecithin.

The method of the present invention allows producing bodies with a surprisingly thick and hence durable shell.

Consequently, the diameter of the shell may be in the range of about 100 nm to 1000 μm, preferably about 300 nm to 3 μm, more preferred about 500 nm to 1 μm.

The body described in the present invention may comprise a protein in the range of about 0.0001-80 weight-%, preferably in the range of about 0.01-1 weight-%, even more preferred in the range of about 0.01-0.3 weight-%.

If the protein content of the body of the present invention is high, e.g., in the range of 10-80 weight-%, this allows the preparation of bodies that—if removed from the composition—have a dry appearance although they contain a liquid core.

Hence, the present invention also relates to a body, comprising 10-80 weight-% of protein carrying a positive or no net charge at the pH of the composition and at least one lipidic phosphatidic acid surfactant, and a content comprising an internal phase containing a hydrophilic component and/or a hydrophobic component.

The bodies described in the present invention may further comprise particles that adsorb on a water/oil interface, are encasted in its shell and protruding at the hydrophobic side of the shell.

Particles that attach to the water/oil interface of the shell irreversibly due to high interfacial energy gain are entrapped at the surface of the shell allowing for further applications.

The capsule or membrane can then be seen as having a functionalized surface, the surface layer of particles hence may be used for controlling physical and chemical interactions with the environment.

Such particles may be any particles that deliver a desired property to the body. For example, such particles may be selected from the group consisting of coloring agents, tastants, antioxidants, antibacterial agents, radical scavengers, fat particles, mineral particles, charged molecules, and combinations thereof.

The composition of the present invention may in principle be used to prepare any kind of product the bodies described in the present invention are considered beneficial for.

For example, the composition of the present invention may be used for the preparation of a food composition, an animal food composition, a pharmaceutical composition, a cosmetic composition, a nutraceutical, a drink, a food additive or a medicament.

The composition of the present invention and/or the bodies described in the present invention offer many advantages as already discussed.

For example, the composition of the present invention and/or the bodies described in the present invention may be used to stabilize emulsions.

The bodies of the present invention exhibit a remarkable stability, which will contribute to the emulsion stability. Further, the surface of the bodies may be functionalized with agents that serve themselves to stabilize emulsions, such as emulsifiers.

The composition of the present invention and/or the bodies described in the present invention may be used to stabilize any kind of emulsions, for example, water in oil (w/o) or oil in water (o/w) emulsions, double emulsions (w/o/w, or o/w/o) or ISAmulsions.

The composition of the present invention may impart many different features and/or functionalities to a product. Essentially this may be achieved by the content of the bodies, by the functionalization of the shell surface of the bodies or by a combination of both means.

For example, the composition of the present invention and/or the bodies described in the present invention may be used to for the preparation of a product with a longer lasting flavour perception.

Advantageously, after oral consumption the bodies described in the present invention will be in contact with the tongue much longer than normal tastants present in a food composition. Tastants, such as mint oil for example, will be released slowly and on site from the content of the bodies, when chewing, for example.

Additionally or alternatively the composition of the present invention and/or the bodies described in the present invention may be used to provide an improved flavour conservation, and/or fragrance conservation.

If present in the bodies or as a functional part of the surfaces of the bodies flavour and/or aroma compounds are significantly less volatile and will remain within the product for significantly longer time periods. They are also protected from unwanted reactions, such as oxidation, for example.

If a tastant or fragrance that provides a refreshing effect is used, the refreshing effect will be improved, because the perceived intensity will be increased and the effect will be prolonged. Tastants or fragrances providing refreshing effects may be mint oil or citrus oils, such as lemon, lime, orange or grapefruit oils, for example. Other etheric oils may be equally well be used.

The composition of the present invention and/or the bodies described in the present invention may be also be used to provide a moisture barrier, for example. In particular, if the bodies have a fibrillar or flat shape, they may be used to protect a product from moisture loss, for example. The bodies will then form a membrane like structure which protects a product.

The composition of the present invention and/or the bodies described in the present invention may also be used to provide an anti-microbial and/or an antifungal activity. The bodies described in the present invention, in particular if they have a flat or fibrillar shape may serve as a moisture barrier. As such, they will automatically prevent microbial or fungal colonization of the product.

Alternatively or additionally, the bodies of any shape may be filled with an antimicrobial and/or antifungal agent. Alternatively or additionally the surface of the shell may be functionalized with an antimicrobial and/or antifungal agent. Such bodies will be effective if they are mixed with a product and also if the composition covers the surface of a product to be protected from microbial or fungal contamination.

The composition comprising the bodies described in the present invention may be prepared by a method comprising the steps of combining the at least one lipidic phosphatidic acid surfactant with the oily fraction to produce a solution A; and combining protein with the hydrophilic fraction to produce a solution B.

Here typically the amount of the at least on one lipidic phosphatidic acid surfactant in the oily fraction is in the range of 0.01% to 1% w/w and the pH may be adjusted to a range of 1.5 to 6.5.

The typical amount of protein in the hydrophilic fraction may be in the range of 0.01% to 1% w/w and the pH may be adjusted to a range of 1.5 to 6.5.

Then either solutions A and B are mixed to prepare dispersion C1; or a dispersion D is prepared of solution A and a hydrophilic solvent and then dispersion D is mixed with solution B to prepare dispersion C2, or a dispersion E is prepared of solution B and a hydrophobic solvent and then dispersion E is mixed with solution A to prepare dispersion C3.

In dispersion C1, A and B may be used in a volume proportion range of 1:1000 to 1:2.

In dispersion D, A and a hydrophilic solvent may be used in a volume proportion range of 1:1000 to 1:2. The pH may be adjusted to a range of 1.5 to 6.5.

In dispersion C2, D and B may be used in a volume proportion range of 1:1000 to 1:2.

In dispersion E, B and a hydrophobic solvent may be used in a volume range of 1:1000 to 1:2. The pH may be adjusted to a range of 1.5 to 6.5.

In dispersion C3, E and A may be used in a volume proportion range of 1:1000 to 1:2.

Then a membrane is allowed to form which will represent the shell of the bodies of the present invention.

Membrane growth may be stopped by means known to those skilled in the art.

If the protein solution is the continuous phase, membrane growth may for example be stopped by flocculation of the solubilised protein—e.g. with anionic water-soluble compounds—, or by adjusting the pH to a value of above superior by 1 unit to the isolectric points of all proteins present in the aqueous phase, and/or by washing out the protein from the continuous phase—e.g. using concentration of the capsules and re-dispersion, or dialysis.

In the case where the lipidic solution is the continuous phase membrane growth may be stopped by washing out the lipidic phosphatidic acid emulsifier from the continuous phase—e.g. using concentration of the capsules and re-dispersion, or dialysis.

The resulting shape of the bodies will be essentially spherical. If a different body shape is desired, flowing, shearing, or squeezing forces may be applied to dispersions C1, C2 or C3. Using such forces flat or elongated shapes may be obtained.

Both, the size of the bodies as well as the thickness of the shells may be controlled.

This may be important if the bodies are used for controlled delivery purposes.

Shell thickness and the body size are parameters that can be used to fine-tune the body for the intended purpose. Since high mechanical properties of the shell can be achieved by choosing the appropriate thickness, e.g., oil-in-water capsules are good candidates for being turned into a powder by spray-drying.

The swelling degree of the wet shell can be influenced by pH, osmotic pressure, and the difference between the pH values at the fabrication stage and at the use stage.

The proposed method can also be used in combination with a specific choice as for the inner phase of the capsules, which may e.g. increase its mechanical strength, or add control parameters to controlled release.

Furthermore, the use of fat particles entrapped at the shell surface, for example, enables the control the shell wetting properties. Colloidal properties of the bodies described in the present invention, as well as mechanical interactions with bodies or molecules of a different nature, will depend on the choice of the particles and on the environment of use, as well as on the size of the bodies and the flexibility of the shell.

The presence of the particles on the shell will not affect significantly the encapsulation properties, since the membrane continuity is maintained at the same lengthscale.

The method of the present invention uses food grade proteins to fabricate in one or a few steps, food grade bodies of tuneable composition, size, and shell thickness that are believed to include lipidic bilayers. More specifically, the food protein is believed to form complexes with an oil-soluble (lipidic) phosphatidic acid emulsifier. The oil-solubility of the anionic emulsifier is a key factor regarding the structure thickness control of the shell. The method allows forming water-in-oil and oil-in-water bodies, and enables the encapsulation of certain oil-soluble or water-soluble molecules, or other active species.

The body size is set by the parameters of the emulsification step (e.g., mechanical stirring, concentrations of surface active species) when mixing oil and water, as was observed using microfluidic and batch emulsification methods.

It is clear to those skilled in the art that they can freely combine all features described in the present application without departing from the scope of the invention as disclosed.

Further advantages and features of the present invention will be apparent from the following Examples and Figures.

FIG. 2 shows the linear interfacial moduli during membrane formation at 23° C., at 0.1 Hz, for:

(1) aqueous phase is a protein solution 1% w/w, pH 2.0, being a mixture 3:1 of β-lactoglobulin rods, β-lactoglobulin monomers/oil phase is MCT oil with lecithin YN 0.5% w/w).

(2) aqueous phase is a protein solution 1% w/w, pH 2.0, of β-lactoglobulin monomers/oil phase is MCT oil with lecithin YN 0.5% w/w.

(3) aqueous phase is a protein solution 1% w/w, pH 2.6, being a mixture 3:1 of β-lactoglobulin rods, β-lactoglobulin monomers/oil phase is MCT oil with lecithin YN 0.5% w/w).

Figure 3:
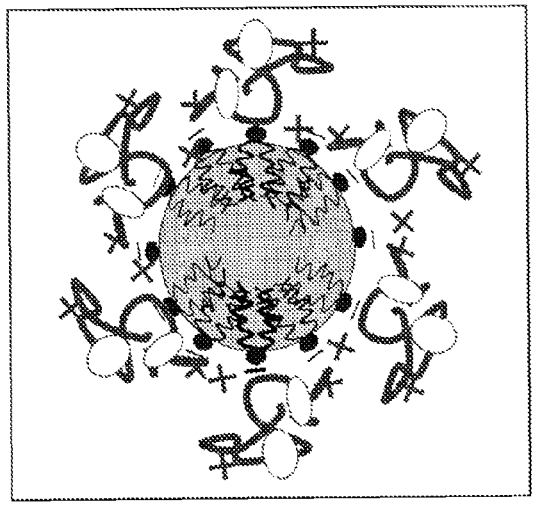
Figure 3:
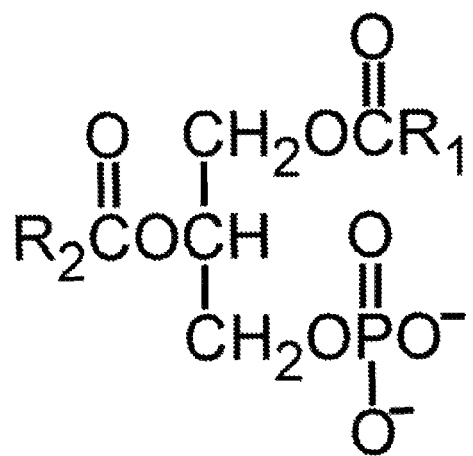

FIG. 3 shows on the left a sketch of the first layer formed by protein/anionic emulsifier complexation at the interface of an oil-in-water drop and on the right the generic chemical structure of phosphatidic acid molecules.

EXAMPLES

Materials

Table 1 shows the interfacial film formation between a solution of 1% w/w of the cited protein or gelatin, at the interface with oil containing 0.5% w/w lecithin YN. Experiments were conducted for the proteins at pH values in the range 1.5-IEP, where IEP is the isoelectric point of the tested protein. Thus for the proteins, the membrane formation is a success for all pH values were it carries either a net positive charge (pH>1.5), or a 0 overall charge. For gelatin, the range 1.5 to 4 was tested, giving a negative result.

|   | Protein or poly electrolyte name | YES | NO |
|---|---|---|---|
| 1 | beta-lactoglobulin monomers | X |  |
| 2 | beta-lac rods, dialyzed | X |  |
| 3 | beta-lac rods, dialyzed and shortened | X |  |
| 4 | caseinate | X |  |
| 5 | Whey Protein Isolates | X |  |

-continued

| | Protein or poly electrolyte name | YES | NO |
|---|---|---|---|
| 6 | Whey Protein Micelles | X | |
| 7 | Soja proteins | X | |
| 8 | Gelatin | | X |

The β-lactoglobulin rods were prepared from solutions of β-lactoglobulin monomers, by heating for 5 hours at 90° C. at pH 2, with a protein concentration of 2% w/w, followed by dialysis to remove the non converted monomers. Their length was in the range 0.5 to 20 µm when not mechanically treated, with a persistence length of the order of 1 µm.

By "shortened rods", we mean that they were treated by high pressure homogenization (700 bar, 5 cycles), which reduced their length to an average value of 200 nm.

Control of Shell Thickness

Microscopy was used to show that shell thickness is growing with time, resulting in a thickening and a strengthening of the interfacial membrane. The shell thickness can thus be controlled by the concentrations in proteins and anions, and the membrane formation time.

Mechanical Properties of the Bodies Shell

Mechanical characterisation of the shell by interfacial shear rheology:

The linear shear interfacial viscoelastic moduli $G'_i$ (storage) and $G''_i$ (loss) of a membrane forming at a flat oil/water interface were characterised (typically at 0.1 Hz) as a function of formation time. The equipment used for recording linear viscoelastic properties of the membrane is an interfacial rheology cell from Anton Paar Physica (Germany), and we used a method to substract the contribution of the bulk phases, as predicted by Boussinesq.

Figure 1:
FIG. 1 shows oil-in-water capsules formed at pH 2.0 for an aqueous phase being a mixture (3:1) of 1% w/w β-lactoglobulin rods and β-lactoglobulin monomers/an oil phase being mid-chain triglyceride oil with 0.5% w/w lecithin YN dissolved.
Figure 1:
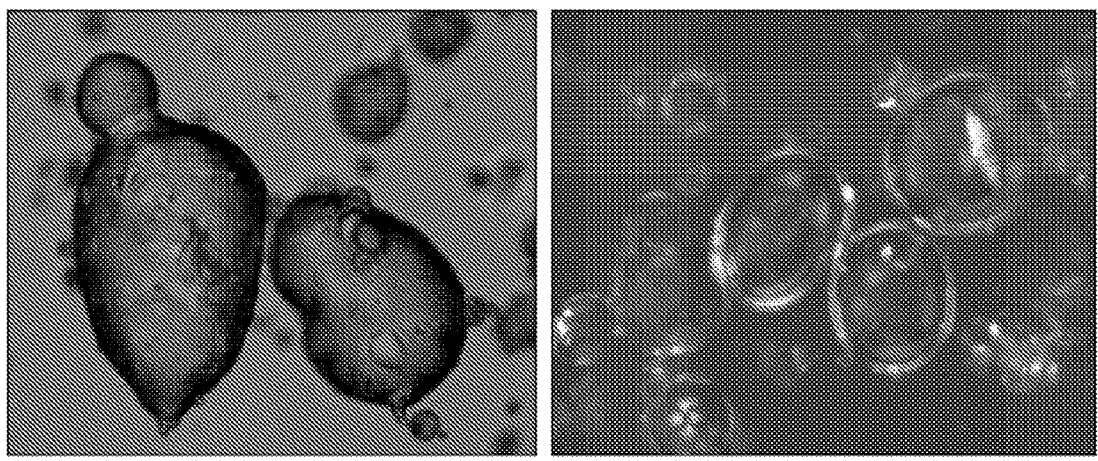
Figure 2:
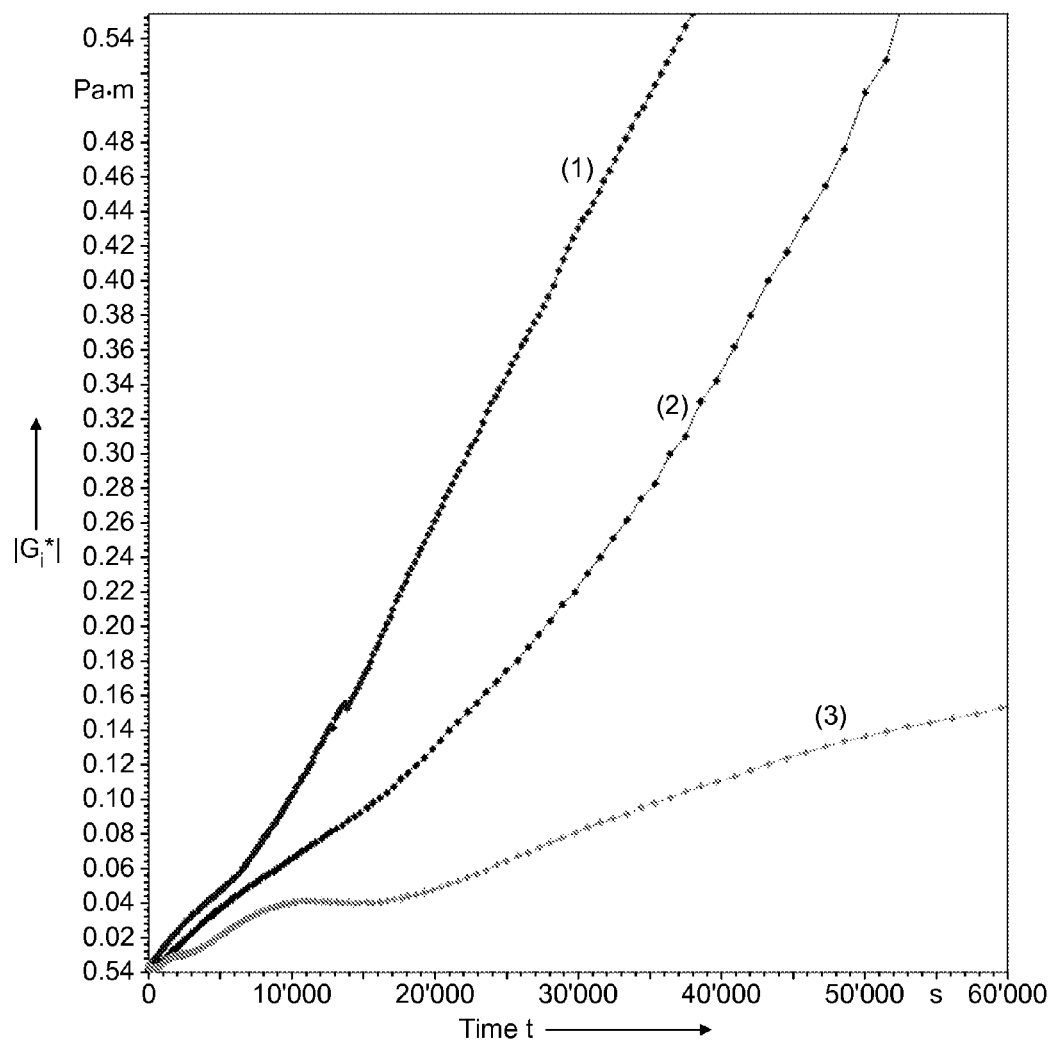

Typical Observations:

High moduli are reached rapidly, compared to both levels of an interface consisting of adsorbed proteins only (based on the same concentration), and an interface consisting of adsorbed lecithin YN (idem), at any waiting time. When the shear modulus achieves the order of 1 Pa·m, the membrane can be easily manipulated with tweezers, displaying high flexibility when in liquid environment and in contact with water (i.e. not dry), i.e. they bend and fold very easily. The high moduli observed support the interpretation of a multi-layered interfacial membrane (see FIG. 2).

Formation of Protein/Lecithin YN Capsules

The protein solutions and dispersions were prepared by classical means starting from protein powders dispersed in distilled water, with adjusting the pH using 1 mol/L or HCl or NaOH.

The lipidic phosphatidic acid used is an ammonium phosphatidic fatty acid comprised in a commercial lecithin lecithin YN, purchased from Palsgaard (Palgaard®4448, food-grade E442, commonly used as viscosity modifier in chocolate formulations). The phosphatidic acids represent more than 50% of all lipidic emulsifiers comprised in lecithin YN. Their generic structure is sketched in FIG. 3 in its anionic form. In FIG. 3, at least one of the groups R1 or R2 is a fatty acid moiety, otherwise a hydrogen atom, and one of the counter-ions is ammonium (not shown). Lecithin YN is insoluble in water at any temperature. It is soluble in common food oils and melted fats up to several grams per liter. The two pKa values of the molecule lecithin YN are 3.0 and 8.0, so when adsorbed at oil/water interface with a pH around 3 or higher, the molecules carry a significant fraction of negative charges; that fraction is 0.25 at pH 3. At pH below the isoelectric point for a given case, the protein molecules carry a net positive charge.

Formation of Protein/Lecithin Oil-in-Water Capsules

1. A protein solution or dispersion (β-lactoglobulin, caseins, whey protein isolates, whey protein microgels, soja proteins, rods of β-lactoglobulin) of a concentration in the range 0.1-1% w/w is prepared by dispersion of a powder of the same protein in water. The pH is set by use of HCl to a value in the range 1.5 to IEP.

2. Lecithin YN is dissolved in mid-chain-triglyceride oil at a concentration in the range 0.1-0.5% w/w.

3. An emulsion is formed by dispersing the lecithin YN oil solution formed in (2) in water at the same pH as the protein solution (dispersion), for oil to water volume proportion typically in the range 1%-40%, using a mechanical dispersion method, typically a high-speed rotor-stator (of e.g. Polytron brand type).

4. The emulsion formed in (3) is mixed with the protein solution (or dispersion) prepared in (1) in 1:1 weight proportions, by soft mechanical mixing.

5. The dispersion formed in (4) is left in quiescent state or kept under gentle mechanical stirring, which leaves the interfacial shell to strengthen mechanically and to grow in thickness.

6. In the dispersion formed in (5), the bodies shell growth is stopped by setting the pH in the aqueous phase to 7 using sodium hydroxide.

Formation of Protein/Lecithin Water-in-Oil Capsules

Water-in-oil capsules can be formed by performing the exact symmetric protocol of the previous Example by changing the role of the oily and aqueous phases, as described hereafter.

1. A protein solution (dispersion) of e.g. the same proteins of the previous example, with a concentration in the range of 0.1-1% w/w, is prepared by dispersion of a powder of the same protein in water. The pH is set by the use of HCl to a value in the range of 1.5 to IEP.

2. Lecithin YN from is dissolved in mid-chain-triglyceride (MCT) oil in a concentration in the range 0.1-0.5% w/w.

3. An emulsion is formed by dispersing the protein solution (dispersion) formed in (1) in mid-chain-triglyceride oil, for a water to oil volume proportion typically in the range of 1%-40%, using a mechanical dispersion method, typically a high-speed rotor-stator (of e.g. Polytron brand type).

4. The emulsion formed in (3) is mixed with the lecithin YN solution prepared in (2) in 1:1 weight proportions, by soft mechanical mixing.

5. The dispersion formed in (4) is left in quiescent state or kept under gentle mechanical stirring, which leaves the interfacial shell to strengthen mechanically and grow in thickness.

6. In the dispersion formed in (5), the capsule shell growth is stopped by successive centrifugation/redispersion steps, with redispersion in pure MCT oil, until the concentration in lecithin YN is low enough for the formation kinetics to be practically stopped at the experimental time scale, e.g. 0.001% w/w.

Formation of Protein/Lecithin Oil-in-Water Fibres

Fibres with a protein/lecithin shell can be formed by applying short duration mechanical forces at the beginning of the shell formation process, as described hereafter. They can be used, e.g., as thickening agent after recovery.

1. A protein solution (dispersion), e.g. of the proteins cited previously, with a concentration in the range of 0.1-1% w/w, is prepared by dispersion of a powder of the same proteins in water. The pH is set by use of HCl to a value in the range 1.5 to IEP.

2. Lecithin YN is dissolved in mid-chain-triglyceride oil in a concentration in the range of 0.1-0.5 weight-%.

3. The lecithin YN solution formed in (2) is dispersed in the protein solution (dispersion) formed in (1) under high stress mechanical stirring using e.g. Polytron rotor-stator. An emulsion is formed by dispersing the lecithin YN oil solution formed in (2) in water at pH in the range of 1.5 to IEP, for an oil to water volume proportion typically in the range of 1%-40%, using a mechanical dispersion method, typically a high-speed rotor-stator (of e.g. Polytron brand type). Since the interfacial tension is very low as soon as the membrane has started forming, the drops are very deformable and are stretched to fibers by the high shear forces.

4. The dispersion formed in (3) is left in quiescent state or kept under gentle mechanical stirring, which leaves the interfacial shell to strengthen mechanically and grow in thickness, and sets the shape of the dispersed oil-in-water bodies to fibers with a biopolymer solid shell.

5. In the dispersion formed in (4), the bodies shell growth is stopped by setting the pH in the aqueous phase to 7 using sodium hydroxide.

6. From dispersion formed in (5), the fibres are recovered by centrifugation/redispersion in pure water.

Formation of a Protein/Lecithin YN Oil-in-Water Capsule with a Composite Shell

Capsules and membranes can be formed in presence of non-ionic emulsifiers, which was tested using mixes of protein monomers and protein aggregates. The results show that the use of mixtures can lead to a surprising strengthening of the shell properties compared to the properties displayed without use of such mixes.

1. A dispersion of 1% w/w proteins consisting of 0.25% w/w β-lactoglobulin monomers and 0.75% w/w of β-lactoglobulin rods is prepared. The pH is set by use of HCl to 2.

2. Lecithin YN is dissolved in mid-chain-triglyceride oil at a concentration in the range of 0.1-0.5% w/w.

3. An emulsion is formed by dispersing the lecithin YN oil solution formed in (2) in water at the same pH as the protein solution (dispersion), for an oil to water volume proportion typically in the range of 1%-40%, using a mechanical dispersion method, typically a high-speed rotor-stator (of e.g. Polytron brand type).

4. The emulsion formed in (3) is mixed with the protein dispersion prepared in (1) in 1:1 weight proportions, by soft mechanical mixing.

5. The dispersion formed in (4) is left in quiescent state or kept under gentle mechanical stirring, which leaves the interfacial shell to strengthen mechanically and to grow in thickness.

6. In the dispersion formed in (5), the capsule shell growth is stopped by setting the pH in the aqueous phase to 7 using sodium hydroxide.

The invention claimed is:

1. A composition comprising an oily fraction, a hydrophilic fraction, and at least one body, the body comprising
a shell comprising at least 20 molecular layers of complex molecules, the complex molecules comprising a protein carrying a positive or no net charge at the pH of the composition and at least one lipidic phosphatidic acid, the lipidic phosphatidic acid surfactant content comprises at least 20% w/w of all lipidic surfactants present in the shell, the diameter of the shell being about 100 nm to 1000 μm, and
a content comprising an internal phase containing at least one of a hydrophilic component and a hydrophobic component.

2. The composition of claim 1, wherein the composition is an emulsion.

3. The composition of claim 1, wherein the protein is selected from the group consisting of β-lactoglobulin caseinates, whey protein isolates, whey protein microgels, soy proteins and combinations thereof.

4. The composition of claim 1, wherein the internal phase comprises at least about 50 Vol-% of the content of the body.

5. The composition of claim 1, wherein the shell comprises a protein and a lipidic phosphatidic acid surfactant having a weight ratio of 1:10 to 10:1.

6. The composition of claim 1, wherein the hydrophilic component of the content is liquid or gaseous.

7. The composition of claim 1, wherein the internal phase comprises at least one oil selected from the group consisting of flavored oil, fragranced oils, mint; essential oils; fish oil; omega-3 fatty acids; and omega-6 fatty acids.

8. The composition of claim 1, wherein the hydrophilic component is selected from the group consisting of hydrophilic liquids, fruit juices, lemonades, alcoholic beverages, coffee liquors, coffee extracts, flavored waters, proteins, enzymes, water-soluble vitamins, and combinations thereof.

9. The composition of claim 1, wherein the body comprises protein carrying a positive or no net charge at the pH of the composition in the range of about 0.00010-80 weight-%.

10. The composition of claim 1, wherein the lipidic surfactant has a partition phosphatidic acid coefficient (water/oil) less than 1:100 in ambient conditions.

11. The composition of claim 1, wherein the body comprises particles that adsorb on a water/oil interface, encasted in its shell and protruding at the hydrophobic side of the shell, wherein the particles are selected from the group consisting of coloring agents, tastants, antioxidants, antibacterial agents, radical scavengers, fat particles, mineral particles, charged molecules, and combinations thereof.

12. A method for the preparation of a product comprising the step of using an oily fraction, a hydrophilic fraction, and at least one body, the body comprising a shell comprising at least 20 molecular layers of complex molecules, the complex molecules comprising a protein carrying a positive or no net charge at the pH of the composition and at least one lipidic phosphatidic acid, the lipidic phosphatidic acid surfactant content comprises at least 20% w/w of all lipidic surfactants present in the shell, the diameter of the shell being about 100 nm to 1000 μm, and a content comprising an internal phase containing at least one of a hydrophilic component or a hydrophobic component to make the product.

13. Method of claim 12, wherein the product provides at least one characteristic selected from the group consisting of a longer lasting flavor perception, an improved flavor, an improved fragrance conservation and an improved refreshing effect.

14. Method of claim 12, wherein the product provides at least one characteristic selected from the group consisting of a moisture barrier, a membrane with an anti-microbial, and an antifungal activity.

15. The composition of claim 1, wherein the composition has a form selected from the group consisting of a substantially round capsule, an elongated capsule, a flat-shape capsule and a fiber.

* * * * *